United States Patent
Gord et al.

(10) Patent No.: US 7,379,774 B2
(45) Date of Patent: May 27, 2008

(54) METHOD AND APPARATUS FOR EFFICIENT POWER/DATA TRANSMISSION

(75) Inventors: John C. Gord, Venice, CA (US); Maria Isabel Arcos-Burgos, Valencia, CA (US); Gregoire Cosendai, Cudrefin (CH)

(73) Assignee: Alfred E. Mann Foundation for Scientific Research, Santa Clarita, CA (US)

( * ) Notice: Subject to any disclaimer, the term of this patent is extended or adjusted under 35 U.S.C. 154(b) by 619 days.

(21) Appl. No.: 10/966,637

(22) Filed: Oct. 14, 2004

(65) Prior Publication Data

US 2005/0085873 A1   Apr. 21, 2005

Related U.S. Application Data

(60) Provisional application No. 60/512,036, filed on Oct. 17, 2003.

(51) Int. Cl.
*A61N 1/00* (2006.01)
(52) U.S. Cl. .................................................. 607/60
(58) Field of Classification Search ................ 607/60, 607/61, 32, 33
See application file for complete search history.

(56) References Cited

U.S. PATENT DOCUMENTS

| | | | |
|---|---|---|---|
| 5,193,539 A | 3/1993 | Schulman | |
| 5,193,540 A | 3/1993 | Schulman | |
| 5,312,439 A | 5/1994 | Loeb | |
| 6,164,284 A | 12/2000 | Schulman | |
| 6,185,452 B1 | 2/2001 | Schulman | |
| 6,208,894 B1 | 3/2001 | Schulman | |
| 6,240,318 B1* | 5/2001 | Phillips | 607/61 |
| 6,315,721 B2 | 11/2001 | Schulman | |
| 6,564,807 B1 | 5/2003 | Schulman | |
| 2002/0032471 A1* | 3/2002 | Loftin et al. | 607/61 |
| 2002/0077672 A1* | 6/2002 | Govari et al. | 607/60 |

FOREIGN PATENT DOCUMENTS

| | | |
|---|---|---|
| EP | 0417634 | 3/1991 |
| EP | 1252911 | 10/2002 |

* cited by examiner

*Primary Examiner*—Scott M Getzow
(74) *Attorney, Agent, or Firm*—Malcolm J. Romano

(57) ABSTRACT

A system, method and power/data transmission device comprising a coil having a high Q, a low-voltage driver and a high-voltage driver switchably coupled to the coil. The low-voltage driver and the high-voltage driver are controlled by a microcontroller and switch at about the same time thereby providing a modulated data signal for transmission. Furthermore, the system includes at least one implantable microstimulator coupled to the transmission device.

20 Claims, 5 Drawing Sheets

METHOD AND APPARATUS FOR EFFICIENT POWER/DATA TRANSMISSION

This application claims the benefit of U.S. Provisional Application No. 60/512,036 filed on Oct. 17, 2003.

FIELD OF THE INVENTION

The present invention is generally directed to an implantable medical device system, and more particularly to a method and apparatus for efficient modulation of data signals and power transmission to the implantable medical device.

BACKGROUND OF THE INVENTION

Transmission of data or information signals is generally achieved through modulation of a carrier signal. The type of modulation, for example, may be amplitude modulation (AM), frequency modulation (FM), or phase modulation. Any of the foregoing modulations can be used depending on the application of the transmission.

A class of implantable medical devices known in the art are small microstimulators and/or sensors. These small microstimulators or sensors, which are hereafter referred to as BION™ devices, are described more fully in the following U.S. Patents: U.S. Pat. No. 5,193,539, entitled "Implantable Microstimulator"; U.S. Pat. No. 5,193,540, entitled "Structure and Method of Manufacture of an Implantable Microstimulator"; U.S. Pat. No. 5,312,439 entitled "Implantable Device Having an Electrolytic Storage Electrode"; U.S. Pat. No. 6,164,284, entitled "System of implantable devices for monitoring and/or affecting body parameters"; U.S. Pat. No. 6,185,452, entitled "Battery-powered patient implantable device"; U.S. Pat. No. 6,208,894, entitled "System of implantable devices for monitoring and/or affecting body parameters "; U.S. Pat. No. 6,315,721, entitled "System of implantable devices for monitoring and/or affecting body parameters"; Pat. No. 6,564,807, entitled "System of implantable devices for monitoring and/or affecting body parameters, each of which patents are incorporated herein by reference. These BION devices are generally small enough to be implanted in a minimally invasive manner through a lumen of a needle, or a similar sized cannula. These BION devices or microstimulators when implanted can provide the appropriate electrical stimulation to the appropriate nerves or muscles in order to rehabilitate or contribute to the functionality of the intended body parts.

Communication with the microstimulators is achieved through a wireless medium. This communication can be through an electromagnetic or RF link or magnetic/inductive coupling of an external device with the microstimulators. In the case of the inductive coupling the external device generally referred to as a BION control unit (BCU) comprises a charger and a controller wherein the functionality of the charger and the controller may be combined and provided through a multi-turn loop antenna in the form of a single coil. This BCU coil is in turn coupled with the coil in the microstimulator providing the inductive coupling and transmission of power and modulated signal to the microstimulator. The communication between the BCU and the BION is through digital communication or pulse modulation of the carrier signal. It has been realized that the sharpness (rise time and/or fall time) of the square wave digital signal can have a direct effect on the communication and the ability of the BION device to properly receive and decode the modulated digital signal. Although a high power modulation amplifier may be used to overcome the problem associated with the low rise time and fall time of a digital square wave pulse modulated signal, however, this would not be compatible with the low power requirements of an implantable microstimulator. It has been further realized that when utilizing a single coil for the transmission of power and modulated signal to microstimulator the use of a high Q coil provides an optimal transmission of power to the microstimulator. However, the use of a high Q coil will adversely affect the modulation signal in that the rise time and the fall time of the signal will be very slow, therefore resulting in an unreliable reception of the modulated signal by the microstimulator. Thus there is a need in the art for an apparatus that comprises a high Q coil and also provides reliable modulation wherein the rise time and the fall time of the modulation signal are adequate for the proper reception by the microstimulator.

BRIEF DESCRIPTION OF THE DRAWINGS

Corresponding numerals indicate corresponding elements throughout the several views of the drawings.

DETAILED DESCRIPTION OF THE PREFERRED EMBODIMENTS

The following description is of the best mode presently contemplated for carrying out the invention. This description is not to be taken in a limiting sense, but is made merely for the purpose of describing the general principles of the invention. The scope of the invention should be determined with reference to the claims.

Figure 1:
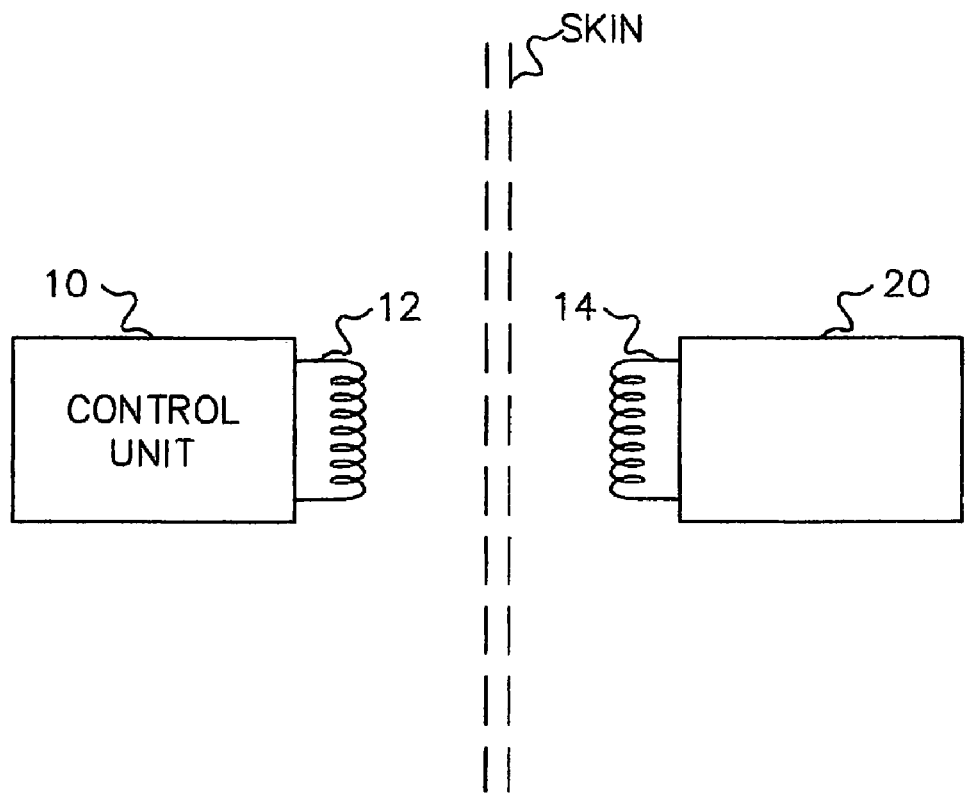
FIG. 1 is an illustration of a functional block diagram of an implantable microstimulator system in accordance with the present invention.

A functional block diagram of an implantable microstimulator/medical device system is illustrated in FIG. 1 in accordance with an embodiment of the present invention. As shown, a control unit 10 is positioned external to the skin of a patient and at least one microstimulator 20 in the form of a BION-type device is provided subcutaneously in the patient's body. The BION devices are approximately less than 6 mm in lateral dimension and less than 60 mm in longitudinal dimension. In the embodiment of the present invention, it is contemplated that the BION devices are less than 2.5 mm in lateral dimension and less than 16 mm in longitudinal dimension. The control unit 10 generally referred to as BION Control Unit (BCU) provides the power and data signals to the microstimulator 20 through a multi-turn loop antenna generally referred to as the external coil 12. In the embodiment of the present invention, the external coil 12 is a high-Q-type coil with low equivalent series resistance. The external coil 12 is made of LITZ wire or any other type of wire known in the art that can provide the high-Q characteristic required for efficient power transmission in an inductively-coupled system. The LITZ wire is characterized as having about 150 strands of 44 gauge electrically conductive wire encased in a silk sheath. One of the design constraints that must be considered when using an implantable device system as shown in FIG. 1 is the efficient transfer of energy to the microstimulator 20. In general, the efficient transfer of energy through an external coil 12 to an internal coil 14 requires the use of a high Q resonant circuit to couple the two coils. A resonant circuit may be described as one containing both inductance (L) and capacitance (C) in which the capacitive reactance is equal to the inductive reactance. This condition occurs at only one frequency in a circuit with fixed constants, and the circuit is said to be "tuned" to this frequency. The "Q" of a resonant circuit may be defined as a figure of merit of the tuned LC circuit, where Q is generally equal to X/R, where X is the reactance of the circuit, and R is the resistance. Because the resistance in a resonant circuit typically represents an energy loss (the loss occurring due to ohmic heating), a more efficient energy transfer occurs when the resistance is low, or the Q is high. Hence, a preferred circuit for coupling energy between a primary coil and an implanted coil will utilize a resonant circuit having a relatively high Q, e.g., a Q greater than or equal to 10. A Q value of twenty or higher is preferred.

When a high Q circuit is used to couple energy between an external coil and an internal coil, the high Q properties of the circuit make it difficult to perform rapid modulation of the carrier signal. Hence, any data modulation signal that also must pass through the high Q resonant circuit tends to exhibit very slow rise and fall times. Disadvantageously, in the context of an implanted medical device system, the integrity of the data transmission (i.e., the ability of the system to reliably detect the data that is transmitted) is significantly adversely affected in proportion to the slowness of the rise and fall times of the modulated data signal.

Figure 2:
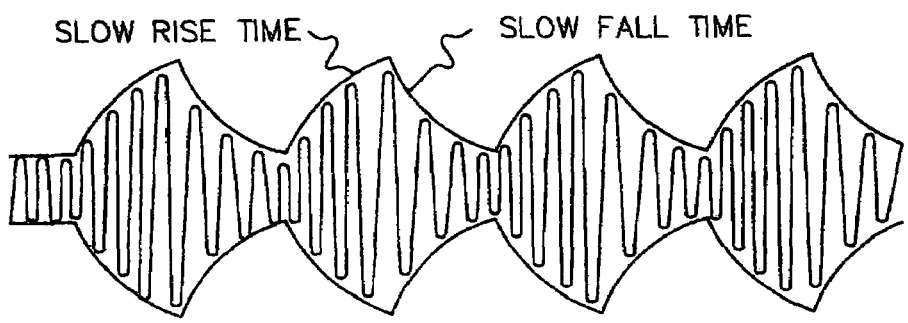
FIG. 2 is an illustration of the slow rise and fall times associated with modulated data signals when utilizing a high-Q coil for transmission of both power and data to the microstimulator.
Figure 2:
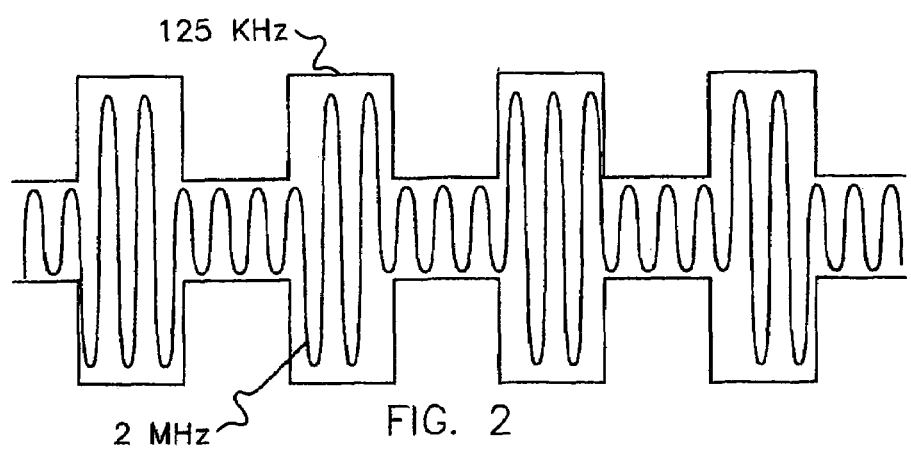

FIG. 2 is an illustration of the contrast between the slow rise and fall times waveform associated with modulated data signals utilizing a high-Q coil for transmission of both power and data to the microstimulator and the proper/desired square waveform for transmission of the data signals. The high-Q coil is highly efficient in transmitting power to the internal coil; however, it is inefficient with respect to the modulation of a data signal for transmission, namely, the higher Q of coil results in the slow rise and fall time of the modulated signal. This in turn adversely affects the sharpness of the modulated data signal which can result in the unreliability of received data signal by the microstimulator 20.

In the present invention, it is contemplated that Manchester encoding may be used to assure reliability. In such encoding, there is always a transition, from high to low or vice versa, at the end of sixteen cycles, which is the bit time. If there is a transition at 8 cycles, the state time, the bit may be termed a "1". If there is no transition at 8 cycles, the bit is then a "0". The Manchester encoding is further discussed in U. S. Pat. No. 5,193,539 which is incorporated herein by reference. The preferred signal modulation in the embodiment of the present invention is amplitude modulation; however, other types of signal modulations can be implemented for various applications.

Figure 3:
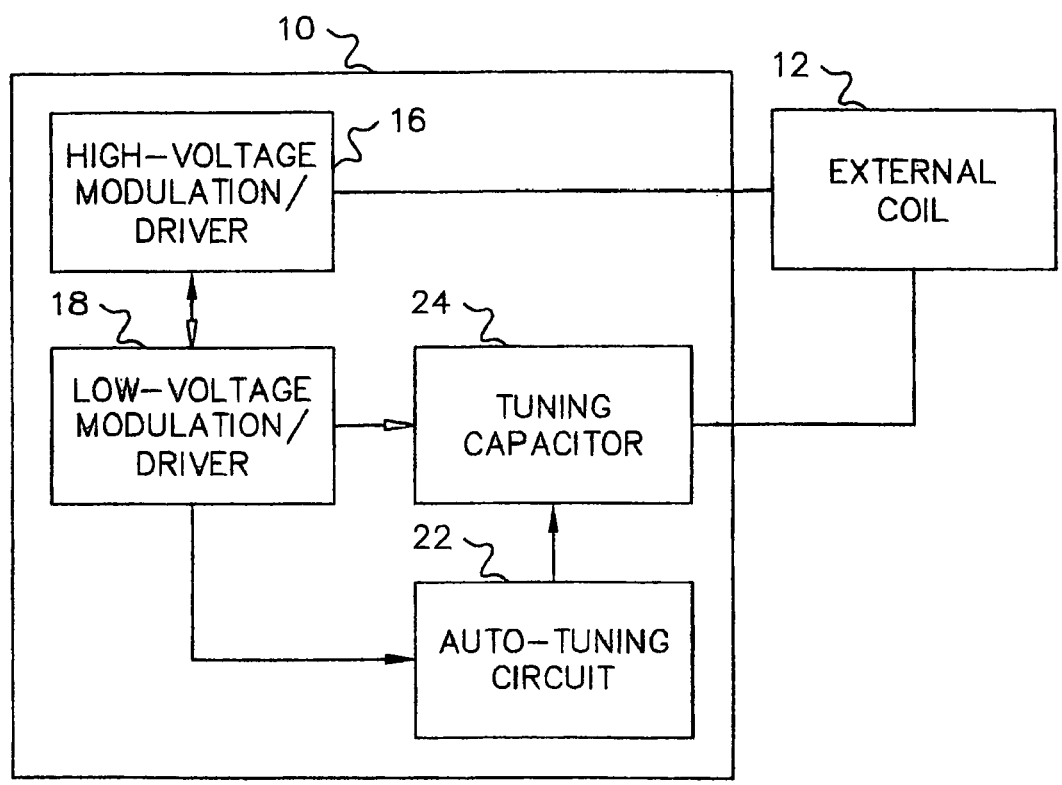
FIG. 3 is an illustration of a block diagram representation of the control unit and the external coil in accordance with the present invention.

FIG. 3 is an illustration of a block diagram representation of the control unit and the external coil in accordance with the present invention. The control unit 10 includes a high-voltage driver 16, a low-voltage driver 18, an auto-tuning circuit 22, and a tuning/adjustable capacitor 24. The auto-tuning circuit 22, for example, can be implemented in the form described in pending patent application Ser. No. 10/429,427 filed on May 5, 2003, titled: "System and Method for Automatic Tuning of a Magnetic Field Generator" which is incorporated herein by reference. In the embodiment of the present invention, the auto-tuning circuit 22, tuning/adjustable capacitor 24 and the external coil 12 form a tuned circuit which is preferably set at 2 MHz of resonant frequency; however, other resonant frequency values may be used depending on the carrier frequency utilized for power transmission. It should be noted that the low equivalent series resistance of the external coil 12 is the resistance that is less than 1/Q times the reactance of the coil at 2 MHz. For example, for a coil of 40 microHenries, the reactance (2.π.f .l ) is about 500 ohms so a coil equivalent series resistance of well less than 5 ohms is appropriate if the desired overall Q is 100. In this example, the equivalent series resistance of less than 5 ohms is desired in order to allow for the other resistances in the circuit such as the impedance of the low and high voltage drivers. The control unit 10 is connected to the external coil 12. The high voltage driver 16 and the low-voltage driver 18 through the tuning capacitor 24 drive the external coil 12.

Traditionally, only a single voltage-driver has been utilized to drive a coil in an inductively-coupled transmission system, especially in an implantable medical device system. As described above, when a high-Q coil is used for both power and data transmission, the modulation of the carrier signal for data signal transmission is adversely affected. The present invention provides a control unit driving a high-Q external coil with a low-voltage and a high-voltage driver concurrently. This arrangement provides for a more reliable modulation of the carrier signal by providing sharp rise times and fall times in square wave data signals.

Figure 4:
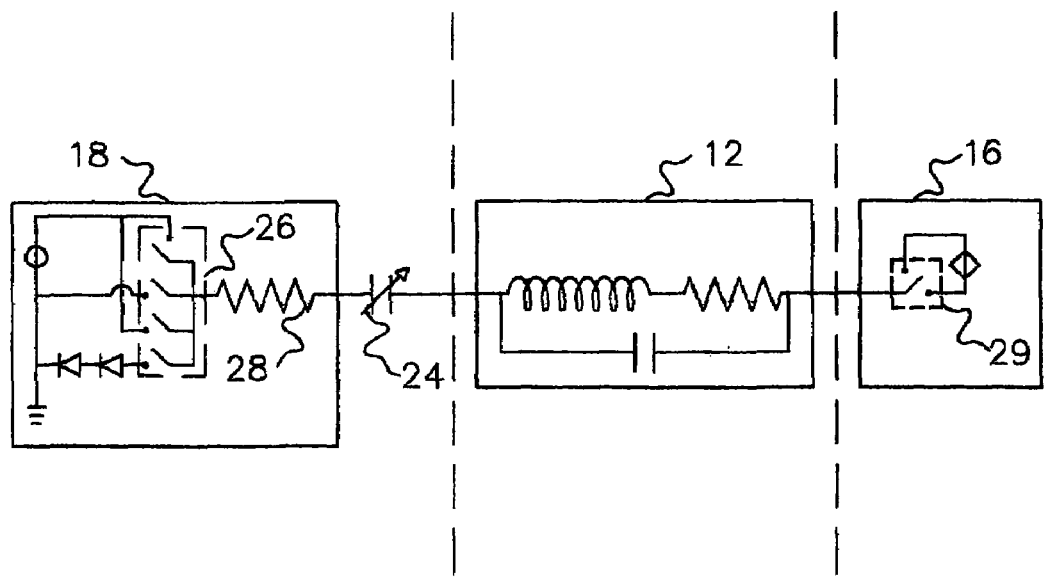
FIG. 4 is an illustration of a high-level schematic representation of the control unit and the external coil in accordance with the present invention.

FIG. 4 is an illustration of a high-level schematic representation of the control unit and the external coil in accordance with the present invention. The low-voltage driver 18 is connected to an auto-tuned circuit broadly represented as adjustable capacitor 24. The low-voltage driver 18 generally includes a switching circuit 26 having at least one switch-mode transistor having a low internal impedance represented by the resistor 28. The adjustable capacitor 24 is controlled by an auto-tuning circuit (not shown). The high-voltage driver 16 generally includes a switching circuit 29 also of a switch-mode transistor type with low impedance that provides the high-voltage input to the external coil 12. As shown in FIG. 4, the external coil 12 includes a parasitic capacitance and resistance. In the embodiment of the present invention, the high-Q external coil 12 has low parasitic capacitance and resistance. The value of the low parasitic capacitance is dependent on the value of the carrier frequency and should be a capacitance that results in a self-resonant frequency well above the carrier frequency. The switching circuits 26 and 29 may be switch-mode transistors or any other switching elements known to those skilled in the art.

Figure 5:
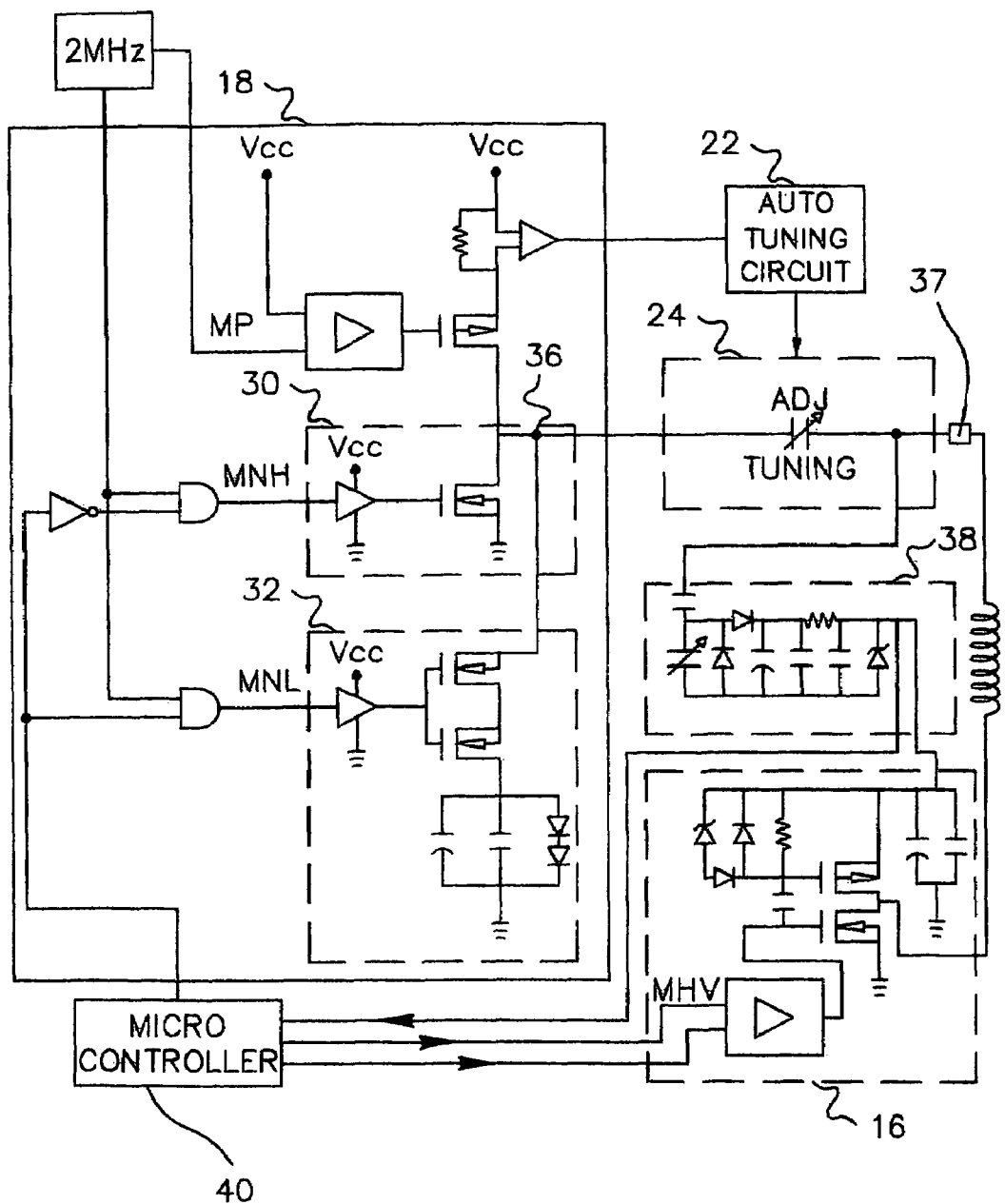
FIG. 5 is an illustration of a detailed schematic representation of the control unit and the external coil in accordance with the present invention.

FIG. 5 is an illustration of a detailed schematic representation of the control unit and the external coil in accordance with the present invention. Referring to FIG. 5, the low-voltage driver 18 provides a change in voltage between approximately 10 volts to the ground and approximately 9 volts to the ground. For example, the Vcc in the circuitry of the low-voltage driver is set at 10 volts. When the switch circuit 30 is closed and the switch circuit 32 is open, then the voltage at the output 36 would be at about 10 volts. In contrast, when the switch circuit 30 is open and the switch circuit 32 is closed, then the output voltage at the output 36 would be at about 9 volts. This transition between 10 volts and 9 volts provides the low-voltage driver modulation to the external coil. The output of the low-voltage modulation is provided to the external coil through the adjustable capacitor 24 which is controlled by the auto-tuning circuit. It should be noted that the tuning of the adjustable capacitor to the external coil may be achieved as described above or through various techniques known to those skilled in the relevant art.

Furthermore, referring to FIG. 5, another advantage of an embodiment of the present invention is achieved wherein the high-voltage driver 16 derives power from a voltage-controlled source 38 which in turn taps off, i.e., is connected to, the transmit resonant circuit. The transmit resonant circuit in the embodiment of the present invention is essentially the combination of the low-voltage driver impedance 28, the adjustable capacitor 24, the external coil 12 including its inductance, parasitic capacitance and parasitic resistance, and the high-voltage driver impedance. The voltage-controlled source 38 is broadly comprised of a capacitor-voltage-division circuitry with the arrangement shown in FIG. 5. It should be noted that the voltage supplied to the high-voltage driver 16 by the voltage-controlled source 38 is dependent on and changes as the impedance of the external coil and hence the Q of the coil changes. The impedance of the external coil changes as the external coil is flexed in various shapes when placed on or near a patient's body. The high-voltage driver provides a proportionately high voltage to the coil based on the Q value of the transmit resonant circuit. For example, if the Q of the external coil is 100, when the external coil is in certain position, and the output voltage of the low-voltage driver is 10 volts, then the voltage at node 37 would be 10×Q=1000 volts. According to the embodiment of the present invention, the modulation provided by the low-voltage driver is about 1 volt which is the difference between the 10 volts and the 9 volts resulting from switching of the switches 30 and 32 (as described above). The 1 volt modulation is 10% modulation of the 10 volts signal of the low-voltage driver 18. Since the high-voltage driver 16 should provide a modulation level corresponding to and concurrently with the modulation provided by the low-voltage driver 18, then the modulation level by the high-voltage driver 16 should also be 10% of the voltage value at node 37. Therefore, in the embodiment of the present invention, the controlled-voltage source 38 provides a voltage division of 10% of the available voltage at node 37 and such that the voltage supplied to the high-voltage driver 16 would be 100 volts. Hence, the high-voltage driver 16 would provide a modulation between 0 volts and 100 volts which is 10% of the voltage supplied as a result of the Q=100 of the transmit resonant circuit. As can be realized from the foregoing example, the voltage supplied by the controlled-voltage source 38 changes with and is dependent on the impedance of the external coil 12 and in turn the Q value of the external coil/transmit resonant circuit. This voltage control of the high-voltage driver insures that the modulation level by the high-voltage driver 16 is appropriate and minimizes transmission error of the modulated data signal. It must be noted that the microcontroller 40 enables the synchronization of the switching of the low-voltage driver 18 and the high-voltage driver 16 in order to provide the proper modulation of the carrier signal. In order to achieve an efficient modulation of the carrier signal, the low-voltage driver and the high-voltage driver should be switched at or near the zero-crossing of the AC coil current.

Figure 6:
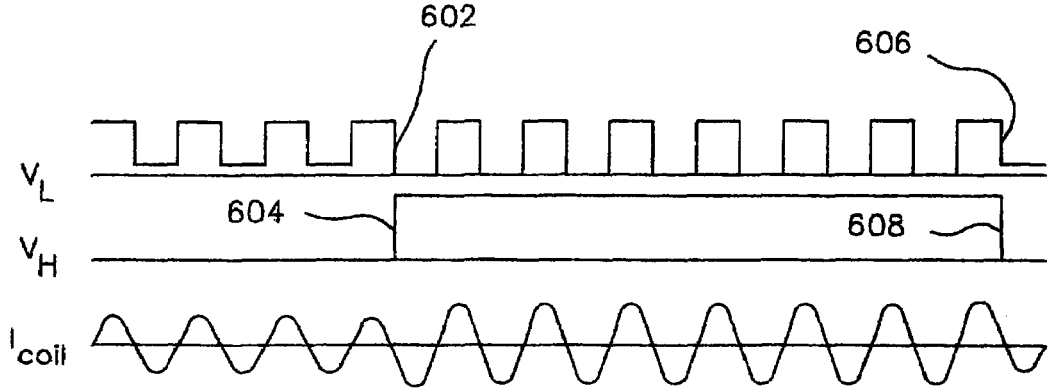
FIG. 6 is an illustration of the waveforms associated with the voltages of the low-voltage driver and the high-voltage driver, and their corresponding modulation of the external coil current in accordance to the principle of the present invention.

FIG. 6 is an illustration of the waveforms associated with the voltages of the low-voltage driver and the high-voltage driver, and their corresponding modulation of the external coil current in accordance to the principle of the present invention. As shown in FIG. 6, the voltage at the output of the low-voltage driver (VL) is provided at the carrier frequency of about 2 MHz. In contrast, the voltage at the output of the high-voltage driver (VH) is provided at a lower frequency corresponding to the modulation frequency of about 125 KHz. According to an embodiment of the present invention, it is contemplated that the high-voltage driver switches at about the same time as one of the switching edges of the low-voltage driver voltage signal. This is accomplished by the microcontroller 40 synchronizing the switching operation of the high-voltage driver and the low-voltage driver such that the high-voltage driver, when modulating, switches at about the same time as one of the switching edges of the low-voltage driver voltage signal. As a result of the foregoing technique, the current through the external coil (Icoil) is accordingly modulated. For example, VL changes from 9 volts to 10 volts (as shown by the edge 602) and at about the same time VH changes from 0 volt to 100 volts (as shown by the edge 604) causing the modulation of the Icoil by a corresponding increase of 10% change in the amplitude of the external coil current. Similarly, at the edge 606, VL changes from 10 volts to 9 volts and VH at about the same time changes to 0 volts causing a corresponding decrease of 10% change in the amplitude of the external coil current.

While the invention has been described by means of specific embodiments and applications thereof, it is understood that numerous modifications and variations could be made thereto by those skilled in the art without departing from the spirit and scope of the invention. It is therefore to be understood that within the scope of the claims, the invention may be practiced otherwise than as specifically described herein.

What is claimed is:

1. A power/data transmission device, comprising:
   a coil having a high Q;
   a low voltage driver capacitively coupled to the coil, said low voltage driver providing a carrier signal at a carrier frequency, said carrier signal defining carrier signal edges; and
   a high voltage driver coupled to the coil, said high voltage driver providing a modulation signal, said modulation signal defining modulation signal edges, wherein the low voltage driver and the high voltage driver together provide a modulated data signal through the coil for transmission to a receiving device and wherein a modulation signal edge is timed to occur at about the same time as a carrier signal edge.

2. The power/data transmission device of claim 1, wherein the coil has a low parasitic capacitance.

3. The power/data transmission device of claim 1, wherein said low voltage driver and said high voltage driver causes an alternating current to flow in the coil, the coil current having zero crossings, a carrier signal edge and a modulation signal edge being timed to occur at a zero crossing.

4. The power/data transmission device of claim 1, wherein the carrier signal is provided at a carrier frequency of about 2 MHz.

5. The power/data transmission device of claim 1, wherein the low voltage driver comprises:
   at least one low impedance switched-mode transistor.

6. The power/data transmission device of claim 1, wherein the high voltage driver comprises:
   at least one low impedance switched-mode transistor.

7. The power/data transmission device of claim 1, wherein a modulation signal edge is synchronized with a carrier signal edge to produce the modulated data signal.

8. The power/data transmission device of claim 1, wherein the modulated data signal is amplitude modulated.

9. A method of power/data transmission, comprising:
   providing a high Q coil;
   capacitively coupling low voltage driver to the coil, the low voltage driver providing a carrier signal at a carrier frequency, the carrier signal defining carrier signal edges;
   coupling a high voltage driver to the coil, the high voltage driver providing a modulation signal, the modulation signal defining modulation signal edges, wherein the low voltage driver and the high voltage driver together provide a modulated data signal through the coil for transmission to a receiving device; and
   timing a modulation signal edge to occur at about the same time as a carrier signal edge.

10. The method of claim 9, wherein coupling the low voltage driver and the high voltage driver the coil, causes an alternating current to flow in the coil, the coil current having zero crossings, further comprising:
    timing a carrier signal edge and a modulation signal edge to occur at a zero crossing.

11. The method of claim 9, wherein the timing comprises:
    synchronizing a modulation signal edge and a carrier signal edge, thereby producing a modulated data signal.

12. The method of claim 9, wherein the carrier frequency is at about 2 MHz.

13. The method of claim 9, wherein the modulation signal amplitude modulates the carrier signal.

14. An implantable medical device system comprising:
    at least one implantable microstimulator;
    a transmission device comprising:
    a coil having a high Q;
    a low voltage driver capacitively coupling a carrier signal, having defined signal edges, to the coil; and
    a high voltage driver coupling a modulation signal, having defined signal edges, to the coil; and
    a receiving device,
    wherein the modulation signal modulates the carder signal and produces an amplitude modulated signal for transmission to the receiving device, and wherein a modulation signal edge is timed to occur at about the same time as a carrier signal edge.

15. The implantable medical device system of claim 14, wherein the at least one microstimulator is less than 60 mm in longitudinal and less than 6 mm in lateral dimension.

16. The implantable medical device system of claim 14, wherein coupling the low voltage driver and the high voltage driver to the coil causes an alternating current to flow in the coil, the coil current having zero crossings, a carrier signal edge and a modulation signal edge being timed to occur at a zero crossing.

17. A method of power/data transmission, comprising:
    providing a high Q coil;
    capacitively coupling a carrier signal to the coil, the carrier signal defining carrier signal edges;
    coupling a modulation signal to the coil, the modulation signal defining modulation signal edges;
    producing a modulated data signal by timing a modulation signal edge to occur at about the same time as a carrier signal edge; and
    transmitting the modulated data signal through the coil to a receiving device.

18. The method of claim 17, wherein coupling the low voltage driver and the high Voltage driver to the coil, causes An alternating current to floW in the coil, the coil current having zero crossings, further comprising:
    timing a carrier signal edge and a modulation signal edge to occur at a zero crossing.

19. The method of claim 17, wherein the carrier frequency is at about 2 MHz.

20. The method of claim 17, wherein the modulation signal amplitude modulates the carrier signal.

* * * * *